US006652889B2

(12) United States Patent
Moore, Jr. et al.

(10) Patent No.: US 6,652,889 B2
(45) Date of Patent: *Nov. 25, 2003

(54) CONCENTRATED AQUEOUS BROMINE SOLUTIONS AND THEIR PREPARATION AND USE

(75) Inventors: Robert M. Moore, Jr., Baton Rouge, LA (US); Christopher J. Nalepa, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/974,622

(22) Filed: Oct. 9, 2001

(65) Prior Publication Data

US 2002/0110603 A1 Aug. 15, 2002

Related U.S. Application Data

(63) Continuation-in-part of application No. 09/404,184, filed on Sep. 24, 1999, now Pat. No. 6,322,822, and a continuation-in-part of application No. 09/506,911, filed on Feb. 18, 2000, now Pat. No. 6,511,682, each is a continuation-in-part of application No. 09/088,300, filed on Jun. 1, 1998, now Pat. No. 6,068,861, said application No. 09/506,911, is a continuation-in-part of application No. 09/404,184.

(51) Int. Cl.$^7$ .................... A01N 39/00; A01N 59/02; A01N 59/08; A01N 59/00
(52) U.S. Cl. .................... 424/703; 424/615; 424/663; 424/665; 424/680; 424/723
(58) Field of Search ................. 424/703, 615, 424/663, 665, 680, 723

(56) References Cited

U.S. PATENT DOCUMENTS

| | | | |
|---|---|---|---|
| 3,152,073 A | 10/1964 | Morton .................... 210/62 |
| 3,170,883 A | 2/1965 | Owen et al. ............. 252/187 |
| 3,308,062 A | 3/1967 | Gunther ................... 210/58 |
| 3,328,294 A | 6/1967 | Self et al. ................ 210/62 |
| 3,558,503 A | 1/1971 | Goodenough et al. ...... 252/187 |
| 3,589,859 A | 6/1971 | Foroulis .................. 21/2.7 |
| 3,711,246 A | 1/1973 | Foroulis .................. 21/2.7 |
| 3,749,672 A | 7/1973 | Golton et al. ............. 252/95 |
| 3,767,586 A | 10/1973 | Rutkiewic ............. 252/187 H |
| 4,032,460 A | 6/1977 | Zilch et al. ........... 252/8.55 B |
| 4,237,090 A | 12/1980 | DeMonbrun et al. ......... 422/13 |
| 4,295,932 A | 10/1981 | Pocius ................... 162/161 |
| 4,382,799 A | 5/1983 | Davis et al. ............... 8/107 |
| 4,427,435 A | 1/1984 | Lorenz et al. .............. 71/67 |
| 4,451,376 A | 5/1984 | Sharp ..................... 210/701 |
| 4,465,598 A | 8/1984 | Darlington et al. ......... 210/721 |
| 4,476,930 A | 10/1984 | Watanabe ................. 166/279 |
| 4,490,308 A | 12/1984 | Fong et al. ............. 260/513 N |
| 4,539,071 A | 9/1985 | Clifford et al. ............ 162/161 |
| 4,546,156 A | 10/1985 | Fong et al. ............... 526/240 |
| 4,566,973 A | 1/1986 | Masler, III et al. ......... 210/701 |
| 4,595,517 A | 6/1986 | Abadi ...................... 252/82 |
| 4,595,691 A | 6/1986 | LaMarre et al. ............ 514/367 |
| 4,604,431 A | 8/1986 | Fong et al. ................ 525/351 |
| 4,642,194 A | 2/1987 | Johnson .................. 210/699 |
| 4,643,835 A | 2/1987 | Koeplin-Gall et al. ....... 210/754 |
| 4,661,503 A | 4/1987 | Martin et al. ............... 514/372 |
| 4,680,339 A | 7/1987 | Fong .................... 525/54.11 |
| 4,680,399 A | 7/1987 | Buchardt .................. 546/139 |
| 4,703,092 A | 10/1987 | Fong ...................... 525/351 |
| 4,711,724 A | 12/1987 | Johnson .................. 210/699 |
| 4,752,443 A | 6/1988 | Hoots et al. ................ 422/13 |
| 4,759,852 A | 7/1988 | Trulear .................. 210/699 |
| 4,762,894 A | 8/1988 | Fong et al. ................ 525/344 |
| 4,777,219 A | 10/1988 | Fong .................... 525/329.4 |
| 4,801,388 A | 1/1989 | Fong et al. ................ 210/701 |
| 4,802,990 A | 2/1989 | Inskeep, Jr. ............... 210/699 |
| 4,822,513 A | 4/1989 | Corby .................... 252/106 |

(List continued on next page.)

FOREIGN PATENT DOCUMENTS

| | | |
|---|---|---|
| EP | 1 080 641 A2 | 3/2001 |
| WO | 9015780 | 12/1990 |
| WO | WO 96/14092 A1 | 5/1996 |
| WO | 9720546 | 6/1997 |
| WO | 9720909 | 6/1997 |
| WO | 9734827 | 9/1997 |
| WO | 9743392 | 11/1997 |
| WO | 9815609 | 4/1998 |
| WO | 9906320 | 2/1999 |
| WO | 9932596 | 7/1999 |
| WO | 9955627 | 11/1999 |
| WO | 00/34186 | 6/2000 |

OTHER PUBLICATIONS

Ault et al., "Infrared and Raman Spectra of the M+Cl,_ ion Pairs and Their Chlorine–bromine Counterparts isolated in Argon Matrices", Journal of Chemical Physics, 1976, vol. 64, No. 12, ppg. 4853–4859.

Willard et al., "Elementary Quantitative Analysis", Third Edition, Chapter XIV, 1933, ppg. 261–271.

Primary Examiner—Alton N. Pryor
(74) Attorney, Agent, or Firm—Edgar E. Spielman, Jr.

(57) ABSTRACT

Described is a process of producing a concentrated liquid biocide formulation. Mixed together are (a) bromine chloride or bromine and (b) an aqueous solution of alkali metal salt of sulfamic acid having a pH of at least about 7, in amounts such that (i) the active bromine content of the solution is at least about 100,000 ppm (wt/wt), and (ii) the atom ratio of nitrogen to active bromine from (a) and (b) is greater than 1 when bromine is used and is greater than 0.93 when bromine chloride is used. Use of bromine chloride as the source of the active bromine in the process is preferred because in the resulting aqueous compositions, all of the bromine of the bromine chloride is made available as active bromine in solution. In other words, the chlorine of the bromine chloride is converted in the process to dissolved alkali metal chloride salt, thereby liberating all of the bromine in the biocidal composition as active bromine capable of providing biocidal activity.

20 Claims, No Drawings

U.S. PATENT DOCUMENTS

| | | | | |
|---|---|---|---|---|
| 4,846,979 A | 7/1989 | Hamilton | ............... | 210/754 |
| 4,883,600 A | 11/1989 | MacDonald et al. | ............... | 210/696 |
| 4,886,915 A | 12/1989 | Favstritsky | ............... | 564/503 |
| 4,898,686 A | 2/1990 | Johnson et al. | ............... | 252/389.2 |
| 4,906,651 A | 3/1990 | Hsu | ............... | 514/372 |
| 4,923,634 A | 5/1990 | Hoots et al. | ............... | 252/389.2 |
| 4,929,424 A | 5/1990 | Meier et al. | ............... | 422/9 |
| 4,929,425 A | 5/1990 | Hoots et al. | ............... | 422/13 |
| 4,966,716 A | 10/1990 | Favstritsky et al. | ............... | 210/755 |
| 4,992,209 A | 2/1991 | Smyk et al. | ............... | 252/387 |
| 4,995,987 A | 2/1991 | Whitekettle et al. | ............... | 210/754 |
| 5,034,155 A | 7/1991 | Soeder et al. | ............... | 252/389.23 |
| 5,035,806 A | 7/1991 | Fong et al. | ............... | 210/701 |
| 5,047,164 A | 9/1991 | Corby | ............... | 252/106 |
| 5,055,285 A | 10/1991 | Duncan et al. | ............... | 423/473 |
| 5,118,426 A | 6/1992 | Duncan et al. | ............... | 210/721 |
| 5,120,452 A | 6/1992 | Ness et al. | ............... | 210/754 |
| 5,120,797 A | 6/1992 | Fong et al. | ............... | 525/329.4 |
| 5,141,652 A | 8/1992 | Moore, Jr. et al. | ............... | 210/754 |
| 5,179,173 A | 1/1993 | Fong et al. | ............... | 525/329.4 |
| 5,192,459 A | 3/1993 | Tell et al. | ............... | 252/106 |
| 5,194,238 A | 3/1993 | Duncan et al. | ............... | 423/473 |
| 5,196,126 A | 3/1993 | O'Dowd | ............... | 210/754 |
| 5,202,047 A | 4/1993 | Corby | ............... | 252/106 |
| 5,259,985 A | 11/1993 | Nakanishi et al. | ............... | 252/180 |
| 5,264,136 A | 11/1993 | Howarth et al. | ............... | 210/754 |
| 5,389,384 A | 2/1995 | Jooste | ............... | 424/661 |
| 5,414,652 A | 5/1995 | Mieda et al. | ............... | 365/122 |
| 5,424,032 A | 6/1995 | Christensen et al. | ............... | 422/14 |
| 5,443,849 A | 8/1995 | Corby | ............... | 424/667 |
| 5,464,636 A | 11/1995 | Hight et al. | ............... | 424/661 |
| 5,525,241 A | 6/1996 | Clavin et al. | ............... | 210/753 |
| 5,527,547 A | 6/1996 | Hight et al. | ............... | 424/661 |
| 5,589,106 A | 12/1996 | Shim et al. | ............... | 252/387 |
| 5,607,619 A | 3/1997 | Dadgar et al. | ............... | 252/187.2 |
| 5,679,239 A | 10/1997 | Blum et al. | ............... | 205/556 |
| 5,683,654 A | 11/1997 | Dallmier et al. | ............... | 422/14 |
| 5,795,487 A | 8/1998 | Dallimier et al. | ............... | 210/754 |
| 5,900,512 A | 5/1999 | Elnagar et al. | ............... | 568/14 |
| 5,922,745 A | 7/1999 | McCarthy et al. | ............... | 514/372 |
| 5,942,126 A | 8/1999 | Dallmier et al. | ............... | 210/756 |
| 6,007,726 A | 12/1999 | Yang et al. | ............... | 210/752 |
| 6,015,782 A | 1/2000 | Petri et al. | ............... | 510/379 |
| 6,037,318 A | 3/2000 | Na et al. | ............... | 510/379 |
| 6,068,861 A * | 5/2000 | Moore et al. | ............... | 424/703 |
| 6,110,387 A | 8/2000 | Choudhury et al. | ............... | 210/752 |
| 6,123,870 A | 9/2000 | Yang et al. | ............... | 252/186.1 |
| 6,156,229 A | 12/2000 | Yang et al. | ............... | 252/186.1 |
| 6,270,722 B1 | 8/2001 | Yang et al. | ............... | 422/37 |
| 6,287,473 B1 | 9/2001 | Yang et al. | ............... | 210/754 |
| 6,322,822 B1 * | 11/2001 | Moore et al. | ............... | 424/703 |

\* cited by examiner

CONCENTRATED AQUEOUS BROMINE SOLUTIONS AND THEIR PREPARATION AND USE

REFERENCE TO RELATED APPLICATION

This is a continuation-in-part of commonly-owned U.S. application Ser. No. 09/404,184, filed Sep. 24, 1999, now U.S. Pat. No. 6,322,822 and Ser. No. 09/506,911, filed Feb. 18, 2000, now U.S. Pat. No. 6,511,682 both of which are continuations-in-part of commonly-owned U.S. application Ser. No. 09/088,300, filed Jun. 1, 1998, now U.S. Pat. No. 6,068,861, issued May 30, 2000. Said application Ser. No. 09/506,911 is also a continuation-in-part of said application Ser. No. 09/404,184.

REFERENCE TO OTHER COMMONLY-OWNED APPLICATIONS

Reference is also made to commonly-owned copending Ser. No. 09/442,025, filed Nov. 17, 1999; Ser. No. 09/451,319, filed Nov. 30, 1999; Ser. No. 09/451,344, filed Nov. 30, 1999; Ser. No. 09/456,781, filed Dec. 8, 1999; Ser. No. 09/663,788, filed Sep. 18, 2000; Ser. No. 09/663,948, filed Sep. 18, 2000; Ser. No. 09/732,601, filed Dec. 7, 2000; and Ser. No. 09/785,890, filed Feb. 16, 2001. The entire disclosures of each of the foregoing eight (8) applications to the extent not in conflict with the present application, are incorporated herein by reference. Reference is also made to commonly-owned copending application No. 09/296,499, filed Apr. 22, 1999, now U.S. Pat. No. 6,110,387, issued Aug. 29, 2000; and Ser. No. 09/658,839, filed Sep. 8, 2000.

BACKGROUND

Bromine-based biocides have proven biocidal advantages over chlorination-dechlorination for the microbiological control of cooling waters and disinfection of waste treatment systems. The water treatment industry recognizes these advantages to be cost-effective control at higher pH values, almost no loss in biocidal activity in the presence of ammonia, and effective control of bacteria, algae and mollusks.

A common way of introducing bromine based biocides into a water system is through the use of aqueous NaBr in conjunction with NaOCl bleach. The user feeds both materials to a common point whereupon the NaOCl oxidizes the bromide ion to $HOBr/OBr^{\ominus}$. This activated solution is then introduced directly into the water system to be treated. The feeding of the two liquids in this fashion is necessary because the $HOBr/OBr^{\ominus}$ mixture is unstable and has to be generated on-site just prior to its introduction to the water. Furthermore, the feeding, and metering of two liquids is cumbersome, especially as the system has to be designed to allow time for the activation of bromide ion to occur. Consequently many biocide users have expressed the need for a single-feed, bromine-based biocide. Elemental bromine and molecular bromine chloride have been considered to meet these demands. Both are liquids at room temperature and can be fed directly to the water system, where immediate hydrolysis occurs to yield HOBr.

(1)

(2)

Properties of bromine and bromine chloride are compared in Table 1.

TABLE 1

Physical Properties of Bromine and Bromine Chloride

| Property | Bromine ($Br_2$) | Bromine Chloride (BrCl) |
|---|---|---|
| Appearance | Fuming, dark-red liquid | Fuming, red liquid or gas |
| Boiling Point | 59° C. | 5° C. |
| Vapor Pressure (25° C.) | 214 mm | 1800 mm |
| Corrosivity | Corrodes most metals in the presence of water | Corrodes most metals in the presence of water |

It can be seen that certain characteristics of these materials—especially their corrosiveness, high vapor pressures and fuming tendencies—necessitate care and skill in their handling and use. Early efforts to overcome the deficiencies of these materials comprised complexing bromine with excess bromide ion in the presence of strong acid and stabilizing the resultant solutions with ethanolamine. The resultant solutions of ethanolammonium hydrogen perbromide contained up to 38% by weight elemental bromine. See in this connection, Favstritsky, U.S. Pat. No. 4,886,915; and Favstritsky, Hein, and Squires, U.S. Pat. No. 4,966,716.

These solutions permitted introduction of bromine to a water system using a single feed. As in the case of bromine and bromine chloride, the ethanolammonium hydrogen perbromide hydrolyzed in water to release HOBr. The vapor pressures of these solutions were lower than elemental bromine and bromine chloride. Nevertheless, the solutions still possessed measurable vapor pressures, and thus tended to produce undesirable reddish-colored vapors during storage and use. An economically acceptable way of stabilizing high concentrations of aqueous solutions of bromine chloride is described in U.S. Pat. No. 5,141,652 to Moore, et al. The solution is prepared from bromine chloride, water and a halide salt or hydrohalic acid. These solutions were found to decompose at a rate of less than 30% per year and in cases of high halide salt concentration, less than 5% per year. Moreover, solutions containing the equivalent of 15% elemental bromine could be prepared. Unfortunately, the relatively high acidity of these solutions and their tendency to be corrosive and fuming impose limitations on their commercial acceptance.

Many solid bromine derivatives such as BCDMH (1,3-bromochloro-5,5-dimethylhydantoin) are limited in the amount of material that can be dissolved in water and fed as a liquid to the water treatment system. For example, the solubility of BCDMH in water is only around 0.15%. Another limitation of such derivatives is that at neutral pH, HOBr rapidly decomposes, eventually forming bromide ions. Thus, the ability to store and transport these aqueous solutions is greatly limited and of questionable commercial feasibility.

U.S. Pat. No. 3,558,503 to Goodenough et al. describes certain aqueous bromine solutions stabilized with various stabilizing agents and various uses to which such solutions can be put. The compositions described in the patent comprise an aqueous bromine solution having from about 0.01 to about 100,000 parts per million by weight of bromine values wherein the molar ratio of bromine to nitrogen present in the bromine stabilizer ranges from about 2.0 to 1 to about 0.5 to 1. The stabilizer used is biuret, succinimide, urea, a lower aliphatic mono- or disubstituted urea containing from about 2 to about 4 carbon atoms in each substituent group, sulfamic acid, or an alkyl sulfonamide of the formula $RSO_3NH_2$ where R is a methyl or ethyl group. The solution also contains sufficient hydroxide additive to provide a pH in the solution ranging from about 8 to about 10, the hydroxide additive being an alkaline earth hydroxide or an alkali metal hydroxide.

U.S. Pat. No. 5,683,654 to Dallmier et al. discusses the preparation of aqueous alkali metal or alkaline earth metal hypobromite solutions by mixing an aqueous solution of alkali or alkaline earth metal hypochlorite with a water soluble bromide ion source to form a solution of unstabilized alkali or alkaline earth metal hypochlorite. To this solution is added an aqueous solution of an alkali metal sulfamate having a temperature of at least 50° C. and in an amount that provides a molar ratio of alkali metal sulfamate to alkali or alkaline earth metal hypobromite of from about 0.5 to about 6 whereby a stabilized aqueous alkali or alkaline earth metal hypobromite solution is formed. The Dallmier et al. patent teaches that much higher levels of available halogen for disinfection were attained by this approach as compared to the Goodenough et al. approach. But the Dallmier et al. patent acknowledges that in their process, the stabilization must occur quickly after the unstable NaOBr is formed.

THE INVENTION

This invention involves a new process of forming concentrated aqueous solutions of biocidally active bromine and in so doing, provides novel and eminently useful concentrated aqueous biocidal solutions of bromine and bromine chloride. Such concentrated solutions can be stored and shipped, and they serve as articles of commerce which, in use, are mixed into the water to be treated for microbiological control. The concentrated aqueous biocidal solutions of this invention are also useful in combating biofilms on surfaces contacted by water. Thus when put to use for microbiological control or biofilm eradication, the concentrated biocidal solutions of this invention are normally diluted in the water being treated. However, in severe cases it is possible to apply a concentrated solution of this invention directly onto a surface infested with biofilm and/or other microbial species or pathogens.

In one of its embodiments this invention provides a process of producing a concentrated liquid biocide composition which comprises mixing (a) bromine chloride or bromine with (b) an aqueous solution of alkali metal salt of sulfamic acid (preferably the sodium salt), the solution having a pH of at least about 7, e.g., in the range of about 10 to about 13.5, and preferably in the range of about 12.5 to about 13.5. The amounts of (a) and (b) used are such that (i) the content of active bromine in the concentrated solution is at least 100,000 ppm (wt/wt) and (ii) the atom ratio of nitrogen to active bromine from (a) and (b) is greater than 1 when bromine is used, and greater than 0.93 when bromine chloride is used. It is preferred that the content of active bromine in the concentrated solution is in the range of from about 145,000 ppm to about 160,000 ppm. It is also preferred, to utilize an atom ratio of nitrogen to active bromine from (a) and (b) that is greater than 1 even when using bromine chloride in the process. In a preferred embodiment the aqueous solution of alkali metal salt of sulfamic acid used in the process is preformed by mixing together in water, (i) sulfamic acid and/or an alkali metal salt of sulfamic acid, and (ii) alkali metal base in proportions such that an aqueous solution of alkali metal salt of sulfamic acid is formed having a pH of at least 7, e.g., in the range of 10 to about 12 or 12.5, and preferably in the range of about 12.5 to about 13.5. If sulfamic acid itself is used as the starting material, it is used initially as a slurry in water with which the alkali metal base is mixed.

When introducing the bromine chloride or bromine into the aqueous solution of alkali metal salt of sulfamic acid, it is desirable to maintain the desired pH of the resulting solution at 7 or above by also introducing into the solution (continuously or intermittently, as desired) additional alkali metal base, such as by a co-feed of an aqueous solution of alkali metal base. When the concentrated aqueous solution is to be stored in drums, it is desirable to have the pH of such solution at about 10 or above, and preferably in the range of about 12.5 to about 13.5.

It is preferred to employ bromine chloride as the source of the active bromine in the above process because in the resulting aqueous compositions, all of the bromine of the bromine chloride is made available as active bromine capable of providing biocidal activity in solution. In other words, the chlorine of the bromine chloride is converted in the process to dissolved alkali metal chloride salt, thereby liberating the bromine as the active bromine content of the biocidal composition which is capable of providing biocidal activity. Thus the more expensive component of the bromine chloride—viz., bromine—is fully utilized in forming active bromine in the aqueous biocidal composition, and concurrently the less expensive component—the anionic chlorine in the bromine chloride—makes this beneficial result possible.

The term "active bromine" of course refers to all bromine-containing species that are capable of biocidal activity. It is generally accepted in the art that all of the bromine in the +1 oxidation state is biocidally active and is thus included in the term "active bromine". As is well known in the art, bromine, bromine chloride, hypobromous acid, hypobromite ion, hydrogen tribromide, tribromide ion, and organo-N-brominated compounds have bromine in the +1 oxidation state. Thus these, as well as other such species to the extent they are present, constitute the active bromine content of the compositions of this invention. See, for example, U.S. Pat. No. 4,382,799 and U.S. Pat. No. 5,679,239. A well-established method in the art for determining the amount of active bromine in a solution is starch-iodine titration, which determines all of the active bromine in a sample, regardless of what species may constitute the active bromine. The usefulness and accuracy of the classical starch-iodine method for quantitative determination of bromine and many other oxidizing agents has long been known, as witness Chapter XIV of Willard-Furman, *Elementary Quantitative Analysis*, Third Edition, D. Van Nostrand Company, Inc., New York, Copyright 1933, 1935, 1940.

A typical starch-iodine titration to determine active bromine is carried out as follows: A magnetic stirrer and 50 milliliters of glacial acetic acid are placed in an iodine flask. The sample (usually about 0.2–0.5 g) for which the active bromine is to be determined is weighed and added to the flask containing the acetic acid. Water (50 milliliters) and aqueous potassium iodide (15% (wt/wt); 25 milliliters) are then added to the flask. The flask is stoppered using a water seal. The solution is then stirred for fifteen minutes, after which the flask is unstoppered and the stopper and seal area are rinsed into the flask with water. An automatic buret (Metrohm Limited) is filled with 0.1 normal sodium thiosulfate. The solution in the iodine flask is titrated with the 0.1 normal sodium thiosulfate; when a faint yellow color is observed, one milliliter of a 1 wt % starch solution in water is added, changing the color of the solution in the flask from faint yellow to blue. Titration with sodium thiosulfate continues until the blue color disappears. The amount of active bromine is calculated using the weight of the sample and the volume of sodium thiosulfate solution titrated. Thus, the amount of active bromine in a composition of this invention, regardless of actual chemical form, can be quantitatively determined.

By utilizing bromine or bromine chloride with caustic in the stabilized bromine composition, higher levels of active halogen are achievable, compared to the levels obtained by the addition of sodium hypochlorite to sodium bromide. The process and the compositions formed also have about twice the content of active bromine as the most concentrated solutions produced pursuant to the Goodenough, et al. patent. Moreover, even at the high levels of active bromine that exist in the compositions of this invention, it has been found possible to provide biocidal compositions that maintain these high levels of active bromine for at least a two-month period, and that do not exhibit a visible or offensive vapor or odor during this period.

In another embodiment, alkali metal dichlorohypobromite, M[BrCl$_2$] (M=alkali metal) is preformed by pre-mixing bromine chloride with aqueous sodium chloride, and the bromine chloride is used in this form to provide the active bromine content of the resultant solution. The preferred alkali metal dichlorohypobromite is sodium dichlorohypobromite.

Another embodiment of this invention is an aqueous biocide composition comprising water having in solution therein (i) an active bromine content derived from bromine chloride of at least about 100,000 ppm (wt/wt), (ii) an alkali metal salt of sulfamic acid (preferably the sodium salt), and (iii) an alkali metal chloride (preferably sodium chloride), wherein the relative proportions of (i) and (ii) are such that the atom ratio of nitrogen to active bromine is greater than 1, and wherein the pH of the composition is at least 7, e.g., in the range of 10 to about 13.5, and preferably in the range of about 12.5 to about 13.5. It is preferred that the content of active bromine in the solution is in the range of from about 145,000 ppm to about 160,000 ppm. In a less preferred embodiment (i) is bromine (Br$_2$) and (iii) is an alkali metal bromide (especially sodium bromide).

The preferred way of forming the above aqueous biocide compositions comprising water having in solution therein an active bromine content of at least about 100,000 ppm (wt/wt), and preferably from about 145,000 ppm to about 160,000 ppm (wt/wt) is to mix together (i) bromine chloride, and (ii) an aqueous solution of alkali metal salt of sulfamic acid, or (iii) water and an alkali metal salt of sulfamic acid, or (iv) water, an alkali metal base, and sulfamic acid, or (v) any combination of (ii), (iii), and (iv), and in relative proportions of such that the atom ratio of nitrogen to active bromine in said biocide composition is greater than 0.93, preferably greater than 1, and the pH of the biocide composition is at least 7 (e.g., in the range of about 10 to about 13.5), and preferably in the range of about 12 or 12.5 to about 13.5.

This invention has made it possible to provide an aqueous biocide composition having a pH of at least 7 and that comprises water having in solution (i) an active bromine content of at least about 100,000 ppm (wt/wt), and (ii) an atom ratio of nitrogen to active bromine of greater than 0.93, the nitrogen originating from sulfamic acid and/or an alkali metal salt thereof, and in which the composition (a) is devoid or essentially devoid of bromate, and (b) since its inception has been devoid or essentially devoid of bromate. By "devoid" of bromate is meant that using the test procedure described hereinafter the level of bromate, if any, is below a detectable amount. Similarly, by "essentially devoid" of bromate is meant that using the test procedure described hereinafter the presence of bromate is confirmed, but that the amount thereof is not more than 50 ppm (wt/wt).

In each of the embodiments of this invention, the atom ratio of nitrogen to active bromine is preferably in the range of about 1.1 to about 1.5, and more preferably in the range of from about 1.35 to about 1.5. Still higher ratios can be employed, if desired.

A further embodiment of this invention is a composition comprising an aqueous solution containing a stable oxidizing bromine compound—i.e., a stabilized active bromine content—wherein the solution is free of detectable bromate. Preferably such composition from its inception is free of detectable amounts of bromate, or in other words, the solution contains at all times from its inception less than 50 ppm of bromate. The stabilized active bromine content of the compositions of this embodiment can be derived from bromine and sulfamic acid or an alkali metal sulfamate such as sodium sulfamate or potassium sulfamate. However, most preferably the stable oxidizing bromine compound is of the type obtainable from bromine or from a combination of bromine and chlorine such as for example, bromine chloride or a mixture of bromine chloride and bromine, and sulfamic acid or an alkali metal sulfamate such as sodium sulfamate. When in the form of a concentrated solution, these compositions contain at least 100,000 ppm (wt/wt), i.e., at least 10 wt %, based on the total weight of the aqueous solution, and most preferably at least about 145,000 ppm (e.g., in the range of about 145,000 to about 160,000 ppm (wt/wt) of active bromine content. Amounts above 160,000 ppm (wt/wt) are also within the scope of this invention. In other words, any concentration of the stabilized active bromine component(s) above about 160,000 ppm (wt/wt) that does not result in precipitate formation during storage or transportation of the concentrated solution under normal ambient temperature conditions constitute compositions of this invention. When used for microbiological control, the concentrated solutions of this invention are mixed or diluted with, or introduced into, additional water, which typically is the water being treated for such microbiological control, so that the amount of active bromine in the water being treated for microbiological control is a microbiologically effective amount. The various compositions of the embodiments referred to in this paragraph preferably additionally contain dissolved chloride ion, most preferably in the presence of a stoichiometric excess of alkali metal cation, such as sodium or potassium cations. In contrast to certain other alkali metal salts, the alkali metal chloride salts have high solubilities in the aqueous medium of the concentrates of this invention, and thus pose no problem with respect to precipitate formation during storage, transportation, or use. In addition, the dissolved alkali metal chloride in the solutions of this invention minimize the extent to which oxygen or air becomes dissolved in the concentrated solutions.

Although not mandatory, it is preferred that from the inception of their production the compositions of this invention are and remain at all times free of peroxides.

Still other embodiments of this invention include the following:

1) A concentrated biocidal composition containing sulfamate-stabilized bromonium ion, such composition (i) from its inception, having a pH in excess of 8 and (ii) having greater than about 10 wt % bromonium ion present, measured as Br$_2$, such wt % being based on the total weight of the composition.
2) A concentrated biocidal composition containing sulfamate-stabilized bromonium ion, such composition (i) containing up to about 16 wt % bromonium ion, measured as Br$_2$, such wt % being based upon the total weight of the composition, (ii) from its inception, being free of detectable amounts of bromate ion, and (iii) from its inception, having a pH greater than 10.

3) A concentrated biocidal composition containing sulfamate-stabilized bromonium ion, such composition (i) containing at least about 10 wt % bromonium ion, measured as $Br_2$, such wt % being based upon the total weight of the composition, (ii) having a pH greater than 10 and (iii) containing no detectable bromate ion.
4) A concentrated biocidal composition containing stabilized oxidizing halogen obtained by the reaction of BrCl and $^\ominus SO_3NH_2$, such composition (i) having up to 16 wt % bromonium ion, measured as $Br_2$, such wt % being based upon the total weight of the composition, and (ii) having a pH greater than 10.
5) A concentrated biocidal composition containing stabilized oxidizing halogen obtained by the reaction of BrCl and $^\ominus SO_3NH_2$, such composition having a pH greater than 10.
6) A concentrated biocidal composition containing stabilized oxidizing halogen obtained by the reaction of BrCl and $^\ominus SO_3NH_2$, such composition containing at least about 10 wt % bromonium ion, measured as $Br_2$, such wt % being based upon the total weight of the composition.
7) A concentrated biocidal composition containing at least about 10 wt % $^\ominus SO_3NH_2$ stabilized non-$BrO^\ominus$-oxidizing halogen.
8) A concentrated biocidal composition containing stabilized non-$BrO^\ominus$-oxidizing halogen, such composition having a pH greater than 10.
9) An aqueous mixture containing stabilized oxidizing halogen and having a pH between about 7 and about 8.

Preferably, but not necessarily, the composition of 1), 2), 3), 7), 8), and 9) immediately above are further characterized by comprising chloride ion in solution therein.

In further embodiments, this invention provides methods for disinfecting surfaces and for sanitizing bodies of water using a bromine-based biocide of this invention. Examples of surfaces that may be disinfected using the methods of this invention include domestic, commercial, industrial, and governmental kitchen counters, tables, floors, and sinks; and bathroom counters, walls, fixtures, and floors. The bodies of water that may be sanitized using the methods of this invention include cooling water systems, waste water effluents, pulp and paper mills, oilfields, air washers, fire reservoirs, and evaporative condensers. These methods use concentrated liquid biocide compositions comprising a biocidally active bromine-based biocide of this invention.

The methods for disinfecting a surface comprise applying to the surface a liquid biocide formed by diluting a concentrate of this invention with an amount of additional water that still contains sufficient biocidally active bromine content to effectively challenge the microorganisms on the surfaces being contacted by the diluted solution. Preferably the diluted solution as applied to the surface contains at least a minimum biofilm eradication concentration (MBEC) of active bromine, which of course will vary somewhat depending upon the biofilm producing species being biocidally challenged. Typical dilutions and methods that can be used for determining MBEC are illustrated in Example 10 hereinafter.

Another embodiment of this invention provides a method of sanitizing a body of water which method comprises introducing into the body of water a liquid biocide composition of this invention. Typically the biocide composition is introduced in concentrated form as received into the body of water. However it is possible to partially dilute the concentrate and to introduce the partially diluted concentrate into the body of water. The amount of the biocide solution, whether used as the original concentrate or as a partially diluted solution formed therewith, should of course contain a sufficient biocidally active bromine content to effectively challenge the microorganisms that are in the body of water being treated and that are on the surfaces that are in contact with or contacted by the body of water being treated. This amount of treating solution used will largely depend on the volume of water being treated and the concentration of the biocide solution being introduced into the water, and to some extent upon the species of microorganisms being challenged. The treated body of water preferably is treated such that it contains at least a minimum inhibitory concentration (MIC) of active bromine. Methods that can be used for determining MIC are illustrated in Example 11 hereinafter.

The organisms that may be controlled using one of the appropriate methods of this invention described above include bacteria, fungi, slime, and mollusks. Advantages resulting from use of the above methods of this invention include the effectiveness of the biocide solutions used, and the facts that the concentrated liquid biocide compositions provided herein are readily dissolved in water, are non-acidic, and are noncorrosive. Moreover sulfamate-stabilized aqueous concentrates when properly prepared pursuant to this invention are devoid or essentially devoid of bromate ion, and preferably contain no detectable bromate ion.

The above and other embodiments of this invention will be still further apparent from the ensuing description and appended claims.

A preferred alkali metal salt of sulfamic acid, and a preferred alkali metal base used in forming such salt are, respectively, potassium sulfamate and a potassium base such as KOH. Most preferred are, respectively, sodium sulfamate, and a sodium base such as NaOH.

One desirable way of accomplishing the mixing of the reactants when producing the concentrated liquid biocide formulations of this invention comprises concurrently introducing (a) bromine chloride and (b) an aqueous solution of alkali metal salt of sulfamic acid into a reaction zone, such as a reactor or other reaction vessel, and having the pH of the resulting solution at least at 7 (e.g., in the range of about 10 to about 13.5), and preferably in the range of about 12 or 12.5 to about 13.5. As noted above, the proportions of (a) and (b) used are such that the active bromine content of the solution is at least about 100,000 ppm (wt/wt), and preferably in the range of about 105,000 to about 120,000 ppm (wt/wt). Concentrated solutions containing as much as from about 145,000 to about 160,000 ppm (wt/wt) can be made and are useful especially when relatively freshly made, but have been found to be less storage stable than desired. Generally speaking, concentrates containing between above about 120,000 and below about 145,000 ppm, have satisfactory storage stability, by not as much as those containing in the range of about 105,000 to about 120,000 ppm (wt/wt). In addition, the proportions of (a) and (b) used are such that all of these concentrates have an atom ratio of nitrogen to active bromine from (a) and (b) that is greater than 0.93, and preferably greater than 1.

A general procedure for preparing the compositions of this invention using sulfamic acid involves, as a first step, forming a slurry of sulfamic acid in water. Typically the pH of this slurry is below 1 pH unit. Sodium hydroxide at 50% concentration is then added until the solid is completely dissolved. Additional 50% NaOH is added until the desired pH is reached. Bromine or bromine chloride is then added at a rate to allow the bromine to dissolve and react with the sulfamic acid without forming a pool of halogen on the bottom of the reactor. On a laboratory scale, a convenient rate of addition is approximately two drops per second. Sodium hydroxide (e.g., 25% or 50%) is co-fed to the reactor to maintain the desired pH (e.g., in the range of 10 to about 13.5, preferably in the range of about 12 or 12.5 to about 13.5, and it may be possible to operate even at a pH in the range of 13.5 to 14. It has been found that stable solutions containing as much as 26% active bromine (11.5% on an active chlorine basis) can be prepared by the process of this invention.

One of the features of this invention is that aqueous biocide compositions are provided that, even though unpurified, are devoid or are essentially devoid of bromate. In other words, if any bromate is present, the amount thereof as determined by use of the test procedure described hereafter is such that the concentrated aqueous biocide compositions of this invention contain bromate in an amount of up to and including (i.e., no greater than) 50 ppm (wt/wt) based on the total weight of the concentrated aqueous biocidal composition. In fact, in preferred concentrated aqueous biocide compositions of this invention this bromate content is in the range of from 0 to about 40 ppm (wt/wt) as determined using such test procedure.

As is known in the art, bromate is a very undesirable component of aqueous systems. For example, U.S. Pat. No. 5,922,745 points out that in 1995 the United States Environmental Protection Agency published a paper identifying some health concerns relevant to bromate formation (G. Amy, et al., Water Supply, 1995, 13(1), 157), and that in the same year animal carcinogenesis was linked to the presence of low levels of bromate in drinking water (J. K. Falwell, and G. O'Neill, Water Supply, 1995, 13(1), 29). While some prior processing achieved reductions in the amount of bromate formed when producing stabilized aqueous bromine-containing biocides, there has remained a need for still further reductions in the amount of bromate present in such biocides. Pursuant to this invention, such further reductions have been made possible. Furthermore, because of this invention, it is now possible to form a concentrated aqueous biocide composition having an active bromine content of at least about 100,000 ppm (wt/wt), and preferably in the range of about 145,000 to about 160,000 ppm (wt/wt), which not only is devoid or essentially devoid of bromate, but which since its inception has been devoid or essentially devoid of bromate. Thus in all stages in the production, handling, storage, transportation, and use of such compositions there is a reduced possibility of exposure to bromate. So far as is known, it has not been possible to achieve such results prior to this invention. Moreover, the water treated pursuant to this invention by addition thereto of an effective biocidal amount of active bromine results in a substantial dilution since, in general, on a wt/wt basis dosages in the treated water in the range of about 0.5 to about 20 parts per million of bromine (expressed as $Br_2$) and preferably in the range of about 4 to about 10 parts per million of bromine (expressed as $Br_2$) in the aqueous medium being treated for biocidal and/or biofilm control will usually suffice. This in turn means that the very small amount of bromate, if any, present in the concentrated aqueous solution of this invention is sharply reduced by orders of magnitude in the water being treated while achieving the microbiological control for which the composition is being used.

Still another feature of this invention is that the invention has made it possible to form a concentrated aqueous biocide composition having an active bromine content of at least about 100,000 ppm (wt/wt), which not only is devoid or essentially devoid of bromate, but which, since its inception, has always had a pH of greater than 8, and preferably in the range of about 12 to about 13.5. Thus it is not necessary to first reduce pH during processing and thereafter to increase the pH of the product solution. Avoidance of such pH adjustments materially simplifies the operations involved in the production of the resultant concentrated aqueous biocide composition of this invention. In addition, when the composition has been maintained at a pH of at least 12 or 13, e.g., in the range of 12 to about 13.5, from its inception, the possibility of bromate formation caused by exposure of the composition to reduced pH is virtually eliminated.

A further advantage of this invention is that it is unnecessary to produce the concentrated aqueous biocide compositions of this invention by use of powerful oxidants such as ozone or peroxides, which are known to possess undesirable, and indeed, hazardous characteristics.

The analytical test procedure to be used for determining the concentration, if any, of bromate in the compositions of this invention is an ion chromatography procedure in which UV detection is employed. The equipment required for the conduct of this procedure is as follows:

a) Ion Chromatograph—Dionex DX-500 or equivalent, equipped with a UV detector and auto sampler.
b) Data Acquisition and Analysis Device—VAX MULTI-CHROM or equivalent chromatography data collection and processing system.
c) Ion Chromatographic Column—Dionex IonPac AG9-HC guard column (p/n 051791) in-line with a Dionex IonPac AS9-HC column (p/n 051786).
d) Volumetric Pipettes—any standard type of suitable volume.
e) Autosampler Vials—1-mL with caps.
f) Volumetric Flasks—100-mL.
g) Syringe—5-cc plastic syringe.
h) Pretreatment Cartridge—OnGuard-H from Dionex (p/n 039596).

The chemicals required for use in the procedure are as follows:
a) Water—Deionized water with a specific resistivity of 17.8 megohm-cm or greater.
b) Sodium Carbonate—"Baker Analyzed"® reagent grade or equivalent.
c) Sodium Bromate—"Baker Analyzed"® reagent grade or equivalent.

The conditions used for the ion chromatograph are as follows:

| | |
|---|---|
| Eluent: | 4.5 millimoles (mM) sodium carbonate |
| Flow-rate | 1.0 mL/minute |
| Injection volume | 50 microliter ($\mu$L) |
| Detector Range | UV at 210 nanometers (nm) |

The eluent is prepared by dissolving 0.4770 gram of the sodium carbonate in 1 liter of the deionized water. These are mixed well and the solution is filtered through a 0.2 IC compatible filter to degas the solution. The concentrated bromate standard solution is prepared by weighing 0.1180 gram±0.001 gram of the sodium bromate into a 100-mL volumetric flask and diluting to volume with deionized water. This produces a solution containing 1,000 micrograms per milliliter of bromate. This concentrated bromate solution should be made fresh at least weekly. The bromate working standard solution is prepared by pipetting 100-microliters of the concentrated bromate standard solution into a 100-mL volumetric flask and filling the flask to volume with deionized water. The solution is mixed well, and yields a standard concentration of 1.0 microgram per milliliter of bromate.

The detailed procedure used for conducting the analysis of an aqueous solution of this invention involves the following steps:
a) Weigh 0.25 gram of the sample solution into a 100-mL volumetric flask. Fill to volume with deionized water and mix well.
b) Flush the OnGuard cartridge with 2-mL of deionized water.
c) Load 5-mL of the sample into the syringe attached to the OnGuard cartridge, pass through at a flow rate of 2 milliliters per minute, and discard the first 3 milliliters. Collect into a 1-mL autosampler vial and cap for analysis.
d) Analyze the samples, making duplicate injections, using the Ion Chromatograph instrument conditions given above.

The calculations involved in the procedure are as follows:
a) Calibration Standard: For bromate, calculate a response factor as follows: R=A/C where R is the response factor, A is the average area counts (2 injections), and C is concentration in micrograms per milliliter ($\mu$g/mL).
b) Samples: ppm bromate=A/(R×W) where A is the average area of sample peak (2 injections), R is the response factor, and W is the weight of the sample in grams.

A method for disinfecting a surface pursuant to this invention comprises applying a concentrated or diluted liquid sulfamate-stabilized biocide composition of the bromine chloride and/or alkali metal dichlorohypobromite to the surface to be disinfected. The liquid biocide composition may be applied to the surface to be disinfected in various ways. The composition may be poured directly onto the surface, sprayed onto the surface, or poured, sprayed or soaked onto an applicator which is then brought into contact with the surface. Applicators include, but are not limited to, cloths, sponges, paper towels, and mops.

A method of sanitizing a body of water pursuant to this invention comprises introducing a concentrated, or partially diluted, liquid biocide composition of sulfamate-stabilized bromine chloride and/or alkali metal dichlorohypobromite into the body of water. A variety of methods may be used to introduce the concentrated liquid biocide composition to the body of water to be sanitized. The concentrated liquid biocide composition may be added directly to the body of water, either all at once or slowly over time, for example via a pump or feeder. In systems in which the water is circulated through an apparatus, the concentrated liquid biocide composition may be added to this apparatus.

The addition of the concentrated liquid biocide composition to the body of water to be sanitized preferably yields a concentration of biocide in the body of water such that in the range of from about 2 to about 10 milligrams per liter of total available halogen, expressed as $Cl_2$, is present in the body of water. In a preferred embodiment, the concentrated liquid biocide composition is introduced into the body of water as required, such that in the range of from about 2 to about 10 milligrams per liter of total available halogen, expressed as $Cl_2$, is maintained within the body of water. A more preferred amount of total available halogen, expressed as $Cl_2$, in the body of water is from about 2 to about 5 milligrams per liter. These concentrations of total available halogen, expressed as $Cl_2$, are ordinarily sufficient for sanitizing a body of water and for maintaining sanitization of a body of water.

This invention provides a process of producing a concentrated liquid biocide composition which comprises mixing (a) bromine chloride with (b) an aqueous solution of alkali metal salt of sulfamic acid (preferably the sodium salt), the proportions of these components being such that the resulting solution has a pH of at least about 7, and preferably in the range of about 12 or 12.5 to about 13.5 or more. Compositions with a pH above about 12 have good shelf-life especially when the active bromine content in the solution is in the range of about 105,000 to about 120,000 ppm (wt/wt), and the atom ratio of nitrogen to active bromine from (a) and (b) is in the range of about 0.93 to about 1.5. Even better properties are obtained with compositions having a pH in the range of about 13 to about 14, an active bromine content in the range of about 145,000 to about 160,000 ppm (wt/wt), and with the atom ratio of nitrogen to active bromine from (a) and (b) in the range of about 1.28 to about 1.54. Bromine chloride is believed to be an equilibrium mixture of bromine chloride molecules, bromine molecules and chlorine molecules.

In a preferred process for producing the concentrated liquid biocide composition, the aqueous solution of alkali metal salt of sulfamic acid used in the process is preformed by mixing together in water, (i) sulfamic acid and/or an alkali metal salt of sulfamic acid, and (ii) alkali metal base in proportions such that an aqueous solution of alkali metal salt of sulfamic acid is formed having a pH of at least 7. If sulfamic acid itself is used as the starting material, it is used initially as a slurry in water with which the alkali metal base is mixed. It is preferred that the alkali metal salt of sulfamic acid is the lithium, sodium, or potassium salt; more preferred are the sodium and potassium salts. Highly preferred as the alkali metal salt of sulfamic acid is the sodium salt.

When mixing the bromine chloride with the aqueous solution of alkali metal salt of sulfamic acid, it is desirable to maintain the desired pH of the resulting solution at 7 or above by also introducing into the solution (continuously or intermittently, as desired) additional alkali metal base, such as by a co-feed of an aqueous solution of alkali metal base.

The use of bromine chloride as the source of the active bromine in the above process is advantageous because in the resulting aqueous compositions, all or essentially all of the bromine of the bromine chloride is made available as active bromine in solution. In other words, the chlorine of the bromine chloride is converted in the process to dissolved alkali metal chloride salt, thereby liberating the bromine as the active bromine content of the biocidal composition. Thus the more expensive component of the bromine chloride— viz., bromine—is fully utilized in forming active bromine in the aqueous biocidal composition, and concurrently the less expensive component—the anionic chlorine in the bromine chloride—makes this beneficial result possible.

By utilizing bromine chloride with caustic in the composition, higher levels of active halogen are achievable compared to the levels obtained by the addition of sodium hypochlorite to sodium bromide. The process and the compositions formed also have about twice the content of active bromine as the most concentrated solutions produced pursuant to the Goodenough, et al. patent. Moreover, even at the high levels of active bromine that exist in the compositions used in this invention, it has been found possible to provide biocidal compositions that maintain these high levels of active bromine for at least a two month period, and that do not exhibit a visible or offensive vapor or odor during this period.

This invention also provides an aqueous biocide composition comprising water having in solution therein (i) an active bromine content derived from bromine chloride of at least about 100,000 ppm (wt/wt), (ii) an alkali metal salt of sulfamic acid, and (iii) an alkali metal chloride, wherein the relative proportions of (i) and (ii) are such that the atom ratio of nitrogen to active bromine in the resultant composition is greater than 1, and the pH of the composition is at least 7, and preferably in the range of about 12 or 12.5 to about 13.5 or more. Again, the preferred alkali metal salt of sulfamic acid is the lithium, sodium, or potassium salt; more preferably, it is the sodium or potassium salt; the most preferred alkali metal salt of sulfamic acid is the sodium salt. Similarly, the alkali metal chloride is preferably lithium chloride, sodium chloride, or potassium chloride; more preferably it is sodium chloride or potassium chloride. Highly preferred as the alkali metal chloride is sodium chloride. In a less preferred embodiment, (iii) is an alkali metal bromide, most preferably sodium bromide.

This invention further provides a process for producing alkali metal dichlorohypobromite, $M[BrCl_2]$ (M=alkali metal), which is preformed by pre-mixing bromine chloride with aqueous alkali metal chloride, and the bromine chloride is used in this form to provide the active bromine content of the biocidal composition. The alkali metal of the alkali metal dichlorohypobromite may be lithium, sodium, potassium, rubidium, or cesium; preferred are lithium, sodium, and potassium; more preferred are sodium and potassium. Sodium dichlorohypobromite is the most preferred alkali metal dichlorohypobromite. Dichlorohypobromite is also referred to in the art as dichlorobromate, bromide dichloride, and dichlorobromide.

To form the biocidal composition, the alkali metal dichlorohypobromite is mixed with an aqueous solution of an alkali metal salt of sulfamic acid which has a pH of at least 7. In the resultant biocidal composition, the atom ratio of nitrogen to active bromine is greater than 0.93. It is preferred that the atom ratio is greater than 1.

In each of the embodiments of this invention, the atom ratio of nitrogen to active bromine in the biocidal composition is preferably in the range of about 1.1 to about 1.5. Still higher ratios can be employed, if desired.

The following examples are presented for purposes of illustration and not limitation.

Various compositions were prepared and the active bromine content of the resultant compositions was determined analytically. The conditions used and results obtained (observations on odor and vapor, and initial contents of active bromine in the solutions) are summarized in Table 2.

Bromine chloride was prepared by adding 20 g of chlorine to 47.0 g of bromine. This bromine chloride was then co-fed with 210 g of 25% sodium hydroxide to maintain the pH between 6 and 8.5 mL of 1 M hydrochloric acid were added to bring the final pH to approximately 7±0.5. The solution, which contained some solids, was transferred to an amber bottle for storage. Starch-iodine titration of a sample of the solution indicated that it had an active bromine concentration of 11.2%.

EXAMPLE 2
Bromine Chloride, Caustic and Sodium Sulfamate

A 1 liter flask was charged with 107 g of sulfamic acid and 200 g of water. Sodium sulfamate was prepared by adding 93.9 g of 50% sodium hydroxide to the stirred slurry. Bromine chloride was prepared by adding 39 g of chlorine to 96.0 g of bromine. This bromine chloride was the co-fed with 319 g of 50% sodium hydroxide to maintain the pH between 11 and 13. After stirring for an additional 30 minutes, the solution, which contained some solids, was transferred to an amber bottle for storage. Starch-iodine titration of a sample of the solution indicated that it had an active bromine concentration of 18.0%. Analysis of the solution after three weeks at ambient temperature indicated that the solution still contained more than 90% of its active bromine content.

EXAMPLE 3
Bromine Chloride, Caustic and Sodium Sulfamate; Larger Scale

A 5 liter flask was charged with 470 g of sulfamic acid and 900 g of water. Sodium sulfamate was prepared by adding 436 g of 50% sodium hydroxide to the stirred slurry. Bromine chloride was prepared by adding 120 g of chlorine to 276 g of bromine. This bromine chloride was then co-fed with 1723 g of 50% sodium hydroxide to maintain the pH between 12 and 13. After stirring for an additional 60 minutes, the orange, clear solution was transferred to an polyethylene bottle for storage. Starch-iodine titration of a sample of the solution indicated that it had an active bromine concentration of 17.6%.

TABLE 2

Data on Prepared Sulfamic Acid Bromine Chloride Solutions

| Ex. No. | Halogen | pH | $SA_{eq}$ | Odor and Vapor Comments | Active $Br_2$, wt %* |
|---|---|---|---|---|---|
| 1** | BrCl | 7 | 0.92 | Strong Br odor, slight fuming | 11.2% |
| 2 | BrCl | 12.5 | 0.94 | Slight sweet smell, no observed vapor | 18.0% |
| 3 | BrCl | 12.8 | 1.41 | Slight sweet smell, no observed vapor | 17.6% |
| 4 | BrCl | 13.5 | 1.35 | | 16.2% |

$SA_{eq}$ = Sulfamic acid to halogen mole ratio.
*Determined by titration using starch-iodine-sodium arsenite method.
**Comparative example.

The specific details for Examples 1–4 of Table 2 are given below. Example 5 illustrates the embodiment of the invention wherein an alkali metal dichlorohypobromite is utilized as the source of active bromine.

EXAMPLE 1
Bromine Chloride, Caustic and Sodium Sulfamate at Neutral pH

A 1 liter flask was charged with 52.0 g of sulfamic acid and 250 g of water. Sodium sulfamate was prepared by adding 60.0 g of 50% sodium hydroxide to the stirred slurry.

EXAMPLE 4
Bromine Chloride, Caustic and Sodium Sulfamate

A 5 liter flask was charged with 390 g of sulfamic acid and 400 g of water. Sodium sulfamate was prepared by adding 1820 g of 25% sodium hydroxide to the stirred slurry while cooling to keep the temperature below 30° C. 344 g of bromine chloride was then added. The orange, clear solution had a pH of 13.5, and was filtered and transferred to a polyethylene bottle for storage. Starch-iodine titration of a sample of the solution indicated that it had an active bromine concentration of 16.2%.

EXAMPLE 5
Reducing Vapor Pressure of Sodium Dichlorohypobromite with Sodium Sulfamate Sodium sulfamate was prepared by slurrying 24.3 g of sulfamic acid in 9 g of water. 24.0 g of 50% sodium hydroxide was added dropwise. The flask heated noticeably and the solid dissolved. This solution was dropped into 184.6 g of sodium dichlorohypobromite. Sodium dichlorohypobromite, Na[BrCl$_2$] is prepared by adding 30.6 g of bromine chloride to 154 g of 3M aqueous sodium chloride. An additional 24 g of 50% sodium hydroxide was added to raise the pH to 7. Analysis of this solution indicated that it had an active bromine concentration of 12.0%.

Various additional compositions were prepared using the above general procedures and the active bromine content of the resultant compositions was determined analytically. The conditions used and results obtained (observations on odor and vapor, and initial contents of active bromine in the solutions) are summarized in Table 3.

TABLE 3

Data on Prepared Sulfamic Acid Stabilized Bromine Solutions

| Ex. No. | Halogen | pH | SA$_{eq}$ | Odor and Vapor Comments | Active Bromine, wt % |
|---|---|---|---|---|---|
| 6 | Br$_2$ | 13.0 | 1.42 | Slight sweet smell, no observed vapor | 12.4%* |
| 7 | Br$_2$ | 7.0 | 1.48 | Slight Br odor, no fuming | 13.4%* |
| 8 | Br$_2$ | 13.0 | 1.15 | Slight sweet smell, no observed vapor | 19.6% |
| 9 | Br$_2$ | 7.0 | 1.13 | Moderate Br odor, no fuming | 26.7% |

SA$_{eq}$ = Sulfamic acid to halogen mole ratio.
*Measured with Hach spectrometer; all others titrated using starch-iodine-sodium arsenite method.
**Comparative example.

The specific details for Examples 8 and 9 are given below. Examples 10 and 11 demonstrate the microbiocidal effectiveness achievable by use of the compositions and methods of this invention.

EXAMPLE 8
Bromine, Caustic (50% Sodium Hydroxide) and Sodium Sulfamate

A 500 mL flask was charged with 26.0 g of sulfamic acid and 50 g water. To this slurry was added 35.0 g of 50% sodium hydroxide. As the acid was converted to the sodium salt, it dissolved into the aqueous solution more readily. Bromine (37.0 g) and 50% sodium hydroxide (30.0 g) were co-fed into the solution at a rate which maintained the pH between 11 and 13. After all of the bromine and caustic had been added, the contents were transferred to an amber bottle for storage. Starch-iodine titration of a sample of the solution indicated that it had an active bromine concentration of 19.6%. Analysis of the bromine solution still contained more than 95% of its active bromine content.

EXAMPLE 9
Bromine, Caustic and Sodium Sulfamate at Neutral pH

A 500 mL flask was charged with 26.0 g of sulfamic acid and 50 g of water. To this stirred slurry was added 30.9 g of 50% sodium hydroxide, which raised the initial pH to approximately 12. The sulfamic acid then dissolved into solution. Bromine (37.7 g) was fed into the solution until the pH dropped to approximately 7, when 50% sodium hydroxide (10.9 g) was co-fed to maintain the pH between 6 and 9.5 mL of 0.01 N sodium hydroxide was used to bring the final pH to approximately 7±0.5. The contents were then transferred to an amber bottle for storage. Starch-iodine titration of a sample of this solution indicated that it had an active bromine content of 26.7%. Analysis of the solution after six weeks of storage at ambient temperature indicated that the stabilized bromine solution still contained more than 95% of its active bromine content.

EXAMPLE 10
Efficacy of BrCl/Sodium Sulfamate Solutions Versus Biofilm (Surface) Bacteria
Biocide Solutions Synthetic water is prepared by adding 0.22 g CaCl$_2$, 0.168 g NaHCO$_3$, and 0.014 g NaCl to 1 L of deionized, distilled water. The mixture is sterilized by filtration through a 0.2 $\mu$m filter. This solution affords water containing 200 ppm calcium hardness (as CaCO$_3$), 150 ppm of alkalinity (as CaCO$_3$), and 150 ppm of chloride, and which has a pH of 8.05.

The stock hypochlorous acid solution is prepared from sodium hypochlorite solution (0.41 g, >4%, actual 2.7%) diluted to 100 g with synthetic water. The solution is stored in a 4 oz. amber glass bottle in the refrigerator. Stock hypobromous acid is blended from sodium hypochlorite (0.42 g, 0.15 mmol) and sodium bromide (0.028 g, 0.27 mmol); this solution is also stored in a 4 oz. amber glass bottle in the refrigerator. 0.0054 g of BrClDMH, 0.0054 g of Br$_2$DMH, and 0.0033 g of trichloroisocyanuric acid are each added with stirring to separate 20 g solutions of synthetic water. The stock BrCl solution is prepared by diluting 0.032 g of the solution from Example 4 with 20 g of synthetic water.

The stock solutions of hypobromous acid (HOBr) and 1,3-bromochloro-5,5-dimethylhydantoin (BrClDMH) were diluted 1:10 for minimum biofilm eradication concentration (MBEC) testing (see below). The stock solutions of BrCl, hypochlorous acid (HOCl), 1,3-dibromo-5,5-dimethylhydantoin (Br$_2$DMH), and trichloroisocyanuric acid were diluted 1:10 and again 1:2.5 for MBEC testing. The solutions are characterized by performing another 1:10 dilution and analyzing for free or total chlorine by the DPD method using a Hach DR 700 spectrophotometer. The actual oxidant levels in the stock solutions prior to their dilution for the MBEC tests are shown in Table 4.

TABLE 4

Oxidant Levels in Solutions for Example 9

| Example | 10a Free Cl$_2$ | 10a Total Cl$_2$ | 10b Free Cl$_2$ | 10b Total Cl$_2$ | 10c Free Cl$_2$ | 10c Total Cl$_2$ |
|---|---|---|---|---|---|---|
| BrCl | | 20.0 | | 37 ppm | | — |
| HOBr | | 10.0 | | 10.1 ppm | | 10.1 |
| HOCl | 10.1 | | 42 ppm | | 10.4 | |
| Br$_2$DMH[a] | | 10.9 | | 40 ppm | | 9.4 |
| BrClDMH[b] | | 9.8 | | 9.1 ppm | | 9.1 |
| Cl$_3$isocyanuric acid[c] | 10.6 | | 44 ppm | | 10.6 | |

[a]Br$_2$DMH = 1,3-dibromo-5,5-dimethylhydantoin
[b]BrClDMH = 1,3-bromochloro-5,5-dimethylhydantoin
[c]Cl$_3$isocyanuric acid = trichloroisocyanuric acid Biofilm Preparation

*Pseudomonas aeruginosa* (ATCC 15442) biofilms, *Klebsiella pneumoniae* (University of Calgary Biofilm Research Group, environmental isolate) biofilms, and mixed biofilms are prepared on the pegs of a plate by aerobic incubation in a simple salts medium with 0.1% glucose (24 hours, 35° C.) containing about 5×10$^6$ cfu/mL bacterial inoculum. The mixed biofilms of *Pseudomonas aeruginosa* and *Klebsiella pneumoniae* are prepared by inoculating 25 mL media with approximately equal amounts of each organism (5×10$^6$ cfu/mL). The 7-day biofilms are prepared by a slight modification of these procedures: each day, spent media was replaced with fresh media and inocula.

Minimum Biofilm Eradication Concentration

The minimum biofilm eradication concentration (MBEC) is defined as the minimum concentration of agent which results in complete biofilm deactivation. The MBEC technique generally consists of growing identical 24-hour biofilms and then challenging the biofilms with decreasing concentrations of selected antibiotics and/or biocides. After a challenge time, the biofilms are placed in wells of growth media and ultra-sonicated to remove any surviving organisms. After incubating overnight, the wells are checked for turbidity. Clear, transparent wells indicate complete deactivation of biofilm bacteria. Conversely, turbidity (growth) indicates incomplete deactivation.

In all cases, the pegs are then rinsed in synthetic water and challenged by the biocide. Following the biocide challenge, the pegs are rinsed twice with synthetic water and then sonicated into Mueller-Hinton broth (225 μL per well). The broth is then incubated for 18 hours at 35° C. MBEC endpoints were unambiguously determined by absorbance at 650 nm. An absorbance >0.100 was considered a positive indication of growth.

Procedure

Both a 24-hour and a 7-day biofilm are prepared from *P. aeruginosa* (Examples 10a and 10b). A 24-hour biofilm is prepared from equal populations of *P. aeruginosa* and *K. pneumoniae* (Example 10c). These biofilms are then challenged with several oxidizing biocides. The 7-day biofilms were more difficult to eradicate than the 24-hour biofilms.

All of the MBEC determinations performed in Example 10 used a pH of 8.0 and a one hour challenge time for the MBEC determination. The results of the minimum biofilm eradication concentration (MBEC) determinations are shown in Table 5.

TABLE 5

MBEC Results for Biofilm Bacteria

| Ex. # | 10a | 10b | 10c |
|---|---|---|---|
| Bacteria | *P. aeruginosa* | *P. aeruginosa* | *P. aeruginosa* and *K. pneumoniae* |
| film growth time | 24 hours MBEC | 7 days MBEC | 24 hours MBEC |
| BrCl | 3.8 ppm | 4.6 ppm | not tested |
| HOBr | 2.5 ppm | 7.6 ppm | 2.5 ppm |
| HOCl | 3.8 ppm | 21 ppm | 2.6 ppm |
| Br$_2$DMH[a] | 1.4 ppm | 5 ppm | 2.4 ppm |
| BrClDMH[b] | 2.4 ppm | 6.8 ppm | 2.3 ppm |
| Cl$_3$isocyanuric acid[c] | 2.0 ppm | 22 ppm | 2.6 ppm |

[a]Br$_2$DMH = 1,3-dibromo-5,5-dimethylhydantoin
[b]BrClDMH = 1,3-bromochloro-5,5-dimethylhydantoin
[c]Cl$_3$isocyanuric acid = trichloroisocyanuric acid

EXAMPLE 11

Efficacy of BrCl/Sodium Sulfamate Solutions versus Planktonic (Solution) Bacteria Biocide Solutions The sodium hypochlorite (NaOCl) solution is an aqueous solution with 5.25% available chlorine. The stock BrCl solution is prepared as in Example 10. Both the NaOCl solution and the BrCl solutions are diluted in a two fold series of dilutions in phosphate buffer at the desired pH for the minimum inhibitory concentration (MIC) tests (see below).

Bacterial Cultures

Cultures of *E. coli*, *P. aeruginosa*, and *S. aureus* are prepared by growing 24-hour cultures of the respective bacteria.

Minimum Inhibitory Concentration

The minimum inhibitory concentration (MIC) is defined as the highest dilution (lowest concentration) which shows complete deactivation of the bacteria. The MIC technique generally consists of growing identical 24-hour bacterial cultures and then challenging a portion of the culture with selected antibiotics and/or biocides. After a challenge time, the challenged portions of the cultures are placed in wells of growth media, and, after incubating overnight, the wells are checked for turbidity. Clear, transparent wells indicate complete deactivation of the bacteria. Conversely, turbidity (growth) indicates incomplete deactivation.

A 0.5 McFarland suspension from a culture is made for minimum inhibitory concentration (MIC) testing. After the challenge time, a 10 μL aliquot is removed to Letheen broth containing 0.1% sodium thiosulfate. The mixture is incubated at 35° C. for 48 hours.

Procedure

The suspensions from the cultures are each challenged separately with NaOCl and BrCl solutions at pH 7 (Examples 11a–c), and with BrCl solutions at pH 8.5 (Examples 11d–11f). 9.9 mL portions of the twofold-diluted biocide solutions were inoculated with 100 μl of a 0.5 MacFarland suspension of a 24-hour culture. After the challenge time, a 10 μL aliquot is removed to Letheen broth containing 0.1% sodium thiosulfate. The mixture is incubated at 35° C. for 48 hours.

All of the determinations performed in Example 11 used a ten minute challenge time for the MIC determination. The results of the minimum inhibitory concentration (MIC) determinations are shown in Table 6.

Another preferred way of operating on a larger scale the process described in the immediately preceding paragraph is in a semi-continuous or semi-batch mode. This involves forming the alkali metal sulfamate solution, preferably a sodium sulfamate solution (using caustic, water, sulfamic acid), and feeding in the bromine chloride or bromine chloride and bromine (BrCl) to a suitable vessel (reactor, tank, etc.) containing the sulfamate solution. The BrCl may go straight into the vessel of the aqueous sodium sulfamate or into a pumparound loop on the vessel. The BrCl may be made up ahead of time, or can be made by continuously mixing the bromine and chlorine together in a pipe, with or without a mixing element, and then injecting it straight into the aqueous sodium sulfamate without isolating the BrCl. The advantage of continuously making the BrCl is that this avoids having a separate BrCl reactor or storage tank and the need for keeping a large quantity of this material in storage on plant facilities.

Besides being useful in the microbiocidal treatment of aqueous media such as recreational water, industrial cooling

TABLE 6

MIC Results for Planktonic Bacteria

| Ex. # | 11a | 11b | 11c | 11d | 11e | 11f |
|---|---|---|---|---|---|---|
| Bacteria | E. coli | P. aeruginosa | S. aureus | E. coli | P. aeruginosa | S. aureus |
| pH | 7 | 7 | 7 | 8.5 | 8.5 | 8.5 |
|  | MIC | MIC | MIC | MIC | MIC | MIC |
| 11 wt % BrCl | 16 ppm | 16 ppm | 16 ppm | 8 ppm | 16 ppm | 16 ppm |
| 5 wt % NaOCl | 8 ppm | 16 ppm | — | — | — | — |

At present, a preferred way of conducting the process of this invention on a larger scale involves charging to a reactor water, aqueous alkali metal hydroxide solution (preferably aqueous sodium hydroxide solution), sulfamic acid, and then bromine chloride or a mixture of bromine chloride and bromine. Preferred proportions of the components are 17 parts by weight of water, 59 parts by weight of a 25 wt % aqueous sodium hydroxide solution, 13 parts by weight of sulfamic acid, and 11 parts by weight of bromine chloride, for a total of 100 parts by weight. Preferably these components are charged in the order named. However, as long as the bromine chloride is charged last, the order of addition of the other three components can be varied. The bromine chloride used preferably contains in the range of 68.9 to 73.1 wt % bromine. However, pure bromine chloride or other combinations of bromine chloride and bromine can be used to make effective product, if desired. The temperature of the mixture during the addition of the bromine chloride is preferably not allowed to exceed 50° C., although the temperature can be allowed to go above 50° C. for short periods of time without detrimental effects. Prolonged exposure to elevated temperatures tends to cause degradation of the product, and thus should be avoided. The bromine chloride concentration in the resultant product solution as formed in this manner (and in whatever chemical form or forms the active bromine chloride exists in such solution), is between 14.5 and 16.0 wt % (i.e., between 145,000 and 160,000 ppm (wt/wt)), and preferably is targeted at about 15.0 wt % (i.e., at about 150,000 ppm (wt/wt)). Determination of such concentration can, of course, be readily accomplished by starch-iodine titration. When operating as described in this paragraph, the final pH of the product solution is in the range of about 12.4 to about 13.7. It will be understood and appreciation that pursuant to this invention an equivalent amount of bromine can be used in this processing in lieu of bromine chloride or mixtures of bromine chloride and bromine.

water, process water, and wastewater, the concentrated solutions of this invention can be used for eradicating, or at least reducing, biofilm on surfaces contacted by aqueous media such as cooling tower surfaces, filter surfaces, surfaces in pools and spas, interior surfaces of pipes and conduits, and similar surfaces on which biofilm can develop. Besides causing damage and/or unsightliness to the surfaces to which the bacterial films become tenaciously attached, biofilms can harbor dangerous pathogens. And because they can form slime layers, biofilms can interfere with normal water flow. Despite the fact that the slimy films themselves constitute protective barriers against penetration of biocidal agents, the biocidal solutions of this invention enable effective biocidal control of biofilms. Thus pursuant to this invention the concentrated aqueous solutions of this invention can be used for introducing biocidally effective amounts of active bromine into aqueous systems that come into contact with surfaces infested with biofilm and thereby at least reduce the biofilm, if not eradicate the biofilm in its entirety. This is of course accomplished by adding an amount of a concentrated (or partially diluted) aqueous solution of this invention to the water to be treated for biofilm reduction or eradication, the amount of such addition being an amount (dosage) that will at least reduce the biofilm, if not eradicate the biofilm in its entirety. Generally speaking, dosages in the range of about 0.5 to about 20 parts per million of active bromine (expressed as $Br_2$) and preferably in the range of about 4 to about 10 parts per million of active bromine (expressed as $Br_2$) in the aqueous medium being treated for biofilm control will usually suffice, but lesser or greater amounts of active bromine can be used whenever deemed necessary, appropriate, or desirable. Naturally there may be some period of time that will pass between the time that the concentrated aqueous solution of this invention is brought into contact with, and thus diluted in, the water being treated, and the time that the biofilm is reduced or eradicated. If desired, such reduction or eradication can be observed by periodically visually inspecting the water-contacted surfaces that are infested with the biofilm, assuming such surfaces are in a location that one can observe. In the case of filters, conduits, or pipes infested with biofilm and carrying water treated pursuant to this invention with a biocidal amount (dosage) of a concentrated aqueous solution of this invention to reduce or eradicate such biofilm, the reduction or eradication of biofilm may be evidenced and thus observed by improved performance of the apparatus (e.g., increased water flow). But whether or not such observations are made, when a biocidally effective amount of active bromine is included in the water that comes in contact with the biofilm after addition to such water of a suitable dosage of a concentrated solution of this invention, reduction or eradication of the biofilm will occur.

This invention also provides a method of disinfecting a surface which comprises applying to such surface a microbiocidally effective amount of an aqueous solution of sulfamate-stabilized liquid biocide formed by dilution of a sulfamate-stabilized active bromine-containing concentrate produced from components consisting essentially of (a) bromine chloride or an alkali metal dichlorohypobromite and (b) an aqueous solution of alkali metal salt of sulfamic acid having a pH of at least 7, and preferably above about 12 (e.g., in the range of 12.5 to 13.5), and most preferably in the range of about 13 to about 14, (a) and (b) being used in amounts such that (i) the active bromine content of said concentrate is at least about 100,000 ppm (wt/wt), most preferably in the range of about 145,000 to about 160,000 ppm, and (ii) the atom ratio of nitrogen to active bromine from (a) and (b) in said concentrate is greater than 0.93, more preferably greater than 1, and most preferably in the range of 1.28 to 1.54. The sulfamate-stabilized active bromine-containing concentrate of this invention can be diluted by any amount of water that does not result in the microbiocidal effectiveness of the diluted solution being lost. Unless the surface requires an even more concentrated dosage to ensure effective microbiocidal control, the solution being applied to the surface will usually be a diluted solution containing a microbiocidally effective amount in the range of about 10 to about 50,000 ppm of active bromine (expressed as $Br_2$). Preferably, the diluted solution for this use will contain a microbiocidally effective amount in the range of about 10 to about 50,000 ppm of active bromine (expressed as $Br_2$). A particularly preferred range of concentration for the diluted concentrate of this invention is a microbiocidally effective amount in the range of about 20 to about 10,000 ppm of active bromine (expressed as $Br_2$).

To determine the amount of active bromine in the water in the low ranges of concentrations described in the immediately preceding two paragraphs, the well-known DPD "total chlorine" test, should be used. While originally designed for analyzing relatively dilute chlorine-containing solutions, the procedure is readily adapted for use in determining active bromine contents of relatively dilute solutions as well. In conducting the test the following equipment and procedure are recommended:

1. The water sample should be analyzed within a few minutes of being taken, and preferably immediately upon being taken.
2. Hach Method 8167 for testing the amount of species present in the water sample which respond to the "total chlorine" test involves use of the Hach Model DR 2010 calorimeter. The stored program number for chlorine determinations is recalled by keying in "80" on the keyboard, followed by setting the absorbance wavelength to 530 nm by rotating the dial on the side of the instrument. Two identical sample cells are filled to the 10 mL mark with the water under investigation. One of the cells is arbitrarily chosen to be the blank. To the second cell, the contents of a DPD Total Chlorine Powder Pillow are added. This is shaken for 10–20 seconds to mix, as the development of a pink-red color indicates the presence of species in the water which respond positively to the DPD "total chlorine" test reagent. On the keypad, the SHIFT TIMER keys are depressed to commence a three minute reaction time. After three minutes the instrument beeps to signal the reaction is complete. Using the 10 mL cell riser, the blank sample cell is admitted to the sample compartment of the Hach Model DR 2010, and the shield is closed to prevent stray light effects. Then the ZERO key is depressed. After a few seconds, the display registers 0.00 mg/L $Cl_2$. Then, the blank sample cell used to zero the instrument is removed from the cell compartment of the Hach Model DR 2010 and replaced with the test sample to which the DPD "total chlorine" test reagent was added. The light shield is then closed as was done for the blank, and the READ key is depressed. The result, in mg/L $Cl_2$ is shown on the display within a few seconds. This is the "total chlorine" level of the water sample under investigation.
3. To convert the result into mg/L active $Br_2$, the result is multiplied by 2.25.

Even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients, or if formed in solution, as it would exist if not formed in solution, all in accordance with the present disclosure. It matters not that a substance, component or ingredient may have lost its original identity through a chemical reaction or transformation during the course of such contacting, blending, mixing, or in situ formation, if conducted in accordance with this disclosure.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. An aqueous biocide composition comprising water having in solution therein an active bromine content of at least about 100,000 ppm (wt/wt), wherein said active bromine content is produced from (i) bromine chloride or a combination of bromine chloride and bromine, and (ii) an aqueous solution of alkali metal salt of sulfamic acid, or (iii) water and an alkali metal salt of sulfamic acid, or (iv) water, an alkali metal base, and sulfamic acid, or (v) any combination of (ii), (iii), and (iv), and in relative proportions of such that the atom ratio of nitrogen to active bromine in said biocide composition is greater than 0.93, and wherein the biocide composition has a pH of at least 10.

2. A composition according to claim 1 wherein said salt of (ii) is a sodium salt of sulfamic acid, wherein said salt of (iii) is a sodium salt of sulfamic acid, and said base of (iv) is a sodium base.

3. A composition according to claim 1 wherein said salt of (ii) is a potassium salt of sulfamic acid, wherein said salt of (iii) is a potassium salt of sulfamic acid, and said base of (iv) is a potassium base.

4. A composition according to any of claims 1–3 wherein said pH is in the range of from about 10 to about 13.5.

5. A composition according to any of claims 1–3 wherein said pH is in the range of from about 12 to about 13.5.

6. A composition according to any of claims 1–3 wherein said atom ratio is greater than 1.

7. A composition according to any of claims 1–3 wherein said atom ratio is greater than 1, wherein said pH is in the range of from about 12.5 to about 13.5.

8. A compositions according to any of claims 1–3 wherein the active bromine content of the solution is in the range of about 145,000 ppm (wt/wt) to about 160,000 ppm (wt/wt).

9. A composition according to any of claims 1–3 wherein said active bromine content is in the range of about 145,000 ppm (wt/wt) to about 160,000 ppm (wt/wt), wherein said atom ratio is greater than 1, wherein said pH is in the range of from about 12 to about 13.5, wherein the bromine chloride of (i) has a bromine content in the range of about 68.9 to about 73.1 wt %, and wherein said bromine chloride is mixed with an aqueous solution of a sodium salt of sulfamic acid.

10. A method of disinfecting a surface which comprises applying to said surface a microbiocidally effective amount of an aqueous solution of sulfamate-stabilized liquid biocide formed by dilution of a sulfamate-stabiized active bromine-containing composition as in any of claims 1–3.

11. A method of sanitizing a body of water which comprises introducing into said body of water a microbiocidally effective amount of a sulfamate-stabilized active bromine-containing composition as in any of claims 1–3.

12. A method of disinfecting a surface which comprises applying to said surface a microbiocidally effective amount of an aqueous solution of sulfamate-stabilized liquid biocide formed by dilution of a sulfamate-stabilized active bromine-containing concentrate produced from components consisting essentially of (a) bromine chloride and (b) an aqueous solution of alkali metal salt of sulfamic acid having a pH of at least 7, (a) and (b) being used in amounts such that (i) the active bromine content of said concentrate is at least about 100,000 ppm (wt/wt), and (ii) the atom ratio of nitrogen to active bromine from (a) and (b) in said concentrate is greater than 0.93.

13. A method according to claim 12 wherein said aqueous solution of alkali metal salt of sulfamic acid is an aqueous solution of the sodium salt of sulfamic acid, wherein the pH of said concentrate is 12.5 to 13.5.

14. A method according to claim 12 wherein said surface before applying said aqueous solution of sulfamate-stabilized liquid biocide has biofilm thereon.

15. A method according to claim 12 wherein said aqueous solution of alkali metal salt of sulfamic acid is an aqueous solution of the sodium salt of sulfamic acid and wherein said atom ratio of said concentrate is greater than 1.

16. A method according to claim 15 wherein the pH of said concentrate is 12.5 to 13.5.

17. A method of sanitizing a body of water which comprises introducing into said body of water a microbiocidally effective amount of a sulfamate-stabilized active bromine-containing concentrate produced from components consisting essentially of (a) bromine chloride and (b) an aqueous solution of alkali metal salt of sulfamic acid having a pH of at least 7, (a) and (b) being used in amounts such that (i) the active bromine content of said concentrate is at least about 100,000 ppm (wt/wt), and (ii) die atom ratio of nitrogen to active bromine from (a) and (b) in said concentrate is greater than 0.93.

18. A method according to claim 17 wherein said surface before applying said aqueous solution of sulfamate-stabilized liquid biocide has biofilm thereon.

19. A method according to claim 17 wherein said aqueous solution of alkali metal salt of sulfamic acid is an aqueous solution of the sodium salt of sulfamic acid and wherein said atom ratio of said concentrate is greater than 1.

20. A method according to claim 19 wherein the pH of said concentrate is 12.5 to 13.5.

* * * * *